US010258457B1

(12) United States Patent
Jweied et al.

(10) Patent No.: US 10,258,457 B1
(45) Date of Patent: Apr. 16, 2019

(54) DYNAMIC DUAL CHAMBER BREATHING PROSTHESIS AND METHODS

(71) Applicants: Ghassan E. Jweied, Potomac, MD (US); Eias E. Jweied, Chicago, IL (US)

(72) Inventors: Ghassan E. Jweied, Potomac, MD (US); Eias E. Jweied, Chicago, IL (US)

(*) Notice: Subject to any disclaimer, the term of this patent is extended or adjusted under 35 U.S.C. 154(b) by 0 days.

(21) Appl. No.: 16/027,322

(22) Filed: Jul. 4, 2018

(51) Int. Cl.
*A61F 2/04* (2013.01)
*A61B 18/00* (2006.01)

(52) U.S. Cl.
CPC ...... *A61F 2/04* (2013.01); *A61B 2018/00541* (2013.01); *A61F 2002/043* (2013.01); *A61F 2210/0057* (2013.01)

(58) Field of Classification Search
CPC ............. A61F 2/04; A61B 2018/00541; A61B 2017/00278
USPC ........................................ 623/9, 23.64–23.65
See application file for complete search history.

(56) References Cited

U.S. PATENT DOCUMENTS

| | | |
|---|---|---|
| 4,643,733 A | 2/1987 | Becker |
| 4,969,898 A | 11/1990 | Calogero |
| 4,969,899 A | 11/1990 | Cox |
| 5,139,527 A | 8/1992 | Redl et al. |
| 5,578,085 A | 11/1996 | Johnson, Jr. et al. |
| 6,653,525 B2 | 11/2003 | Ingenito et al. |
| 9,610,150 B2* | 4/2017 | Flanagan ............... A61F 2/04 |
| 9,974,814 B2 | 5/2018 | Katane et al. |
| 2002/0165618 A1* | 11/2002 | Ingenito ............... A61F 2/0063 623/23.65 |
| 2008/0275295 A1 | 11/2008 | Gertner |
| 2010/0305715 A1* | 12/2010 | Mathis ............... A61B 1/2676 623/23.65 |
| 2013/0223702 A1* | 8/2013 | Holsing ............... A61B 5/113 382/128 |
| 2015/0272591 A1 | 10/2015 | Folan et al. |

FOREIGN PATENT DOCUMENTS

| | | |
|---|---|---|
| CN | 205126494 U | 4/2016 |
| RU | 2533969 C1 | 11/2014 |
| WO | WO 93/10723 | * 10/1993 |

* cited by examiner

*Primary Examiner* — Suzette J Gherbi
(74) *Attorney, Agent, or Firm* — PK Patent Law

(57) ABSTRACT

A dynamic dual chamber breathing prosthesis and methods are provided. The dual chamber breathing prosthesis can include an elastic lung prosthetic capable of being implanted in a chest cavity of a patient in place of an excized portion of lung, such as a lobe, and a reservoir capable of being implanted in the patient. A tube can be configured to be operatively arranged between the elastic lung prosthetic and the reservoir such that the elastic lung prosthetic is in fluid communication with the reservoir. As a breathing cycle including an inspiration phase and an expiration phase alternatingly occur during normal respiration, a fluid is capable of being dynamically transferred between the elastic lung prosthetic and the reservoir during each breathing cycle.

26 Claims, 4 Drawing Sheets

DYNAMIC DUAL CHAMBER BREATHING PROSTHESIS AND METHODS

FIELD OF THE INVENTION

The present teachings relate to a prosthetic device to prevent hyper-expansion of lung tissue. In particular, the present teachings relate to a prosthetic that occupies the portion of a chest cavity left vacant after excision of a portion of a lung or of an entire lung, or to improve pulmonary function in a patient with emphysema, with or without lung resection.

BACKGROUND OF THE INVENTION

As shown in FIG. 1, when a lobectomy is performed a space 10 is created in a chest cavity 18 by the removal of the unhealthy lobe. Removal of the lobe typically results in the diaphragm 14 rising as the remaining healthy lung 16 attempts to fill the newly created space 10. The remaining healthy lung 16 will hyper-expand to an extent to either partially or fully fill the excess space 10. Such a hyper-expansion interferes with normal respiration of the patient as will be discussed in more detail below. A similar lung hyper-expansion can also occur with patients suffering from emphysema, a lung disease. As a result of this lung hyper-expansion, patients can experience exertional dyspnea which can be extremely uncomfortable, limits one's activity, and potentially can become life-threatening.

Referring to FIG. 2, a standard spirometry chart is shown which depicts lung volumes. It is believed that with a lobectomy (or with emphysema) there is not only a decrease in Vital Capacity (VC) and Inspiratory Reserve Volume (IRV) but patients also experience an increase in the Residual Volume (RV) of the remaining native lung (which is essentially and functionally a physiologic dead space), as well as a decrease in Expiratory Reserve Volume (ERV). The increase in RV of the remaining lung corresponds to the hyper-expansion of the remaining healthy lung. The hyper-expansion of the remaining lung also partially accounts for the decrease in ERV and IRV. A similar phenomenon of lung hyperexpansion occurs with emphysema except that in this case the whole lung is diseased and no lung has been removed.

To prevent the remaining lung (or lobe(s)) from hyper-expanding under these situations, it has been described that one may implant a prosthetic into the chest cavity to help restore the normal size, shape, and mechanics of the remaining native lung tissue and allow for more normal respiration to be achieved.

In particular, known implantable lung prosthetics placed in the chest function essentially as static space occupiers that do not change in their size and shape. The problem with known lung prosthetics is that the remaining native lung tissue with which the prosthetic works is not static in size and shape. During normal respiration, native lung tissue will change in size and shape from about 12 to about 20 times a minute. At the same time, the chest cavity within which the native lung and lung prosthetic reside also changes in size and shape about 12 to about 20 times per minute during respiration.

With known static-sized lung prosthetics, it is postulated that with inspiration (when the chest cavity increases in size and volume) the lung prosthetic will become surrounded by empty space or the remaining native lung hyperexpands to fill that extra space. Then, with deep expiration (when the chest cavity decreases in size and volume) the same lung prosthetic can become too big for the reduced sized space that it occupies. As a result, during normal respiration known implanted lung prosthetics do not mimic the change in lung size and volume of the excised lung or the change in size and volume of the chest cavity.

Another known implanted prosthetic includes a pressure relieving area which provides a place for excess fluid to decompress as a safety measure during changes in thoracic pressure, such as during an airplane flight. However, this known prosthetic design does not allow fluid to pass into and out of the prosthetic as the patient breathes during normal respiration. As a result, known implanted lung prosthetics having pressure relieving areas also do not mimic the change in lung shape and size that occurs during normal respiration.

As such, known implanted prosthetics do not effectively prevent the exacerbation of perturbations in physiologic lung volumes (such as Residual Volume (RV), Expiratory Reserve Volume (ERV), and Inspiratory Reserve Volume (IRV)) and therefore are incapable of properly ameliorating exertional dyspnea that patients can experience.

Accordingly, there exists a need for a prosthesis that can change in size and shape as the patient breathes in and out so as to mimic the operation of a real lung during normal respiration while at the same time filling out the chest cavity as the chest changes in size and volume during respiration.

SUMMARY OF THE INVENTION

The present teachings provide a dual chamber breathing prosthesis including an elastic lung prosthetic capable of being implanted in a chest cavity of a patient in place of excised lung tissue. The dual chamber breathing prosthesis further includes a reservoir capable of being implanted in the patient and a tube configured to be operatively arranged between the elastic lung prosthetic and the reservoir such that the elastic lung prosthetic is in fluid communication with the reservoir. As a breathing cycle including an inspiration phase and an expiration phase alternatingly occurs during normal respiration, a fluid is capable of being dynamically transferred between the elastic lung prosthetic and the reservoir during each breathing cycle.

The present teachings also provide a dual chamber breathing prosthesis device capable of dynamically changing in size during a breathing cycle of a patient defined by an inspiration phase and an expiration phase. The dual chamber breathing prosthesis device includes an elastic lung prosthetic capable of being implanted in a chest cavity of the patient, an elastic reservoir capable of being implanted in the patient, and a tube configured to place the elastic lung prosthetic in fluid communication with the elastic reservoir. During each breathing cycle, the elastic lung prosthetic is configured to dynamically change in size whereby during the inspiration phase the elastic lung prosthetic increases in size and during the expiration phase the elastic lung prosthetic decreases in size.

The present teachings still further provide a surgical method for improving pulmonary function of a remaining native lung during normal respiration of a patient after a lung resection surgery. The surgical method includes implanting an elastic lung prosthetic in a chest cavity of the patient in the vicinity of the remaining native lung, implanting an elastic reservoir in the patient, and providing a tube to arrange the elastic lung prosthetic in fluid communication with the elastic reservoir. The surgical method further includes providing a fluid within the reservoir and allowing a dynamic change in size of the elastic lung prosthetic by the fluid transferring from the elastic reservoir into the elastic lung prosthetic by a force created by an inspiration phase of respiration by the patient and then transferring the fluid from the elastic lung prosthetic back into the elastic reservoir by a force created by an expiration phase of respiration by the patient.

The present teachings yet further provide a surgical method for improving pulmonary function of an emphysematous lung during normal respiration of a patient. The surgical method includes implanting an elastic lung prosthetic in a chest cavity of the patient in the vicinity of the emphysematous lung, implanting an elastic reservoir in the patient, and providing a tube to arrange the elastic lung prosthetic in fluid communication with the elastic reservoir. The surgical method further includes providing a fluid within the reservoir and allowing a dynamic change in size of the elastic lung prosthetic by the fluid transferring from the elastic reservoir into the elastic lung prosthetic by a force created by an inspiration phase of respiration by the patient and then transferring the fluid from the elastic lung prosthetic back into the elastic reservoir by a force created by an expiration phase of respiration by the patient The present teachings even still further provide a surgical method for improving pulmonary function during normal respiration of a patient after a pneumonectomy. The surgical method includes implanting an elastic lung prosthetic in a chest cavity of the patient where the pneumonectomy occurred, implanting an elastic reservoir in the patient, and providing a tube to arrange the elastic lung prosthetic in fluid communication with the elastic reservoir. The surgical method further includes providing a fluid within the reservoir and allowing a dynamic change in size of the elastic lung prosthetic by the fluid transferring from the elastic reservoir into the elastic lung prosthetic by a force created by an inspiration phase of respiration by the patient and then transferring the fluid from the elastic lung prosthetic back into the elastic reservoir by a force created by an expiration phase of respiration by the patient.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

It is to be understood that both the foregoing general description and the following detailed description are exemplary and explanatory only, and are intended to provide an explanation of various embodiments of the present teachings.

DETAILED DESCRIPTION OF THE PREFERRED EMBODIMENTS

Figure 3:
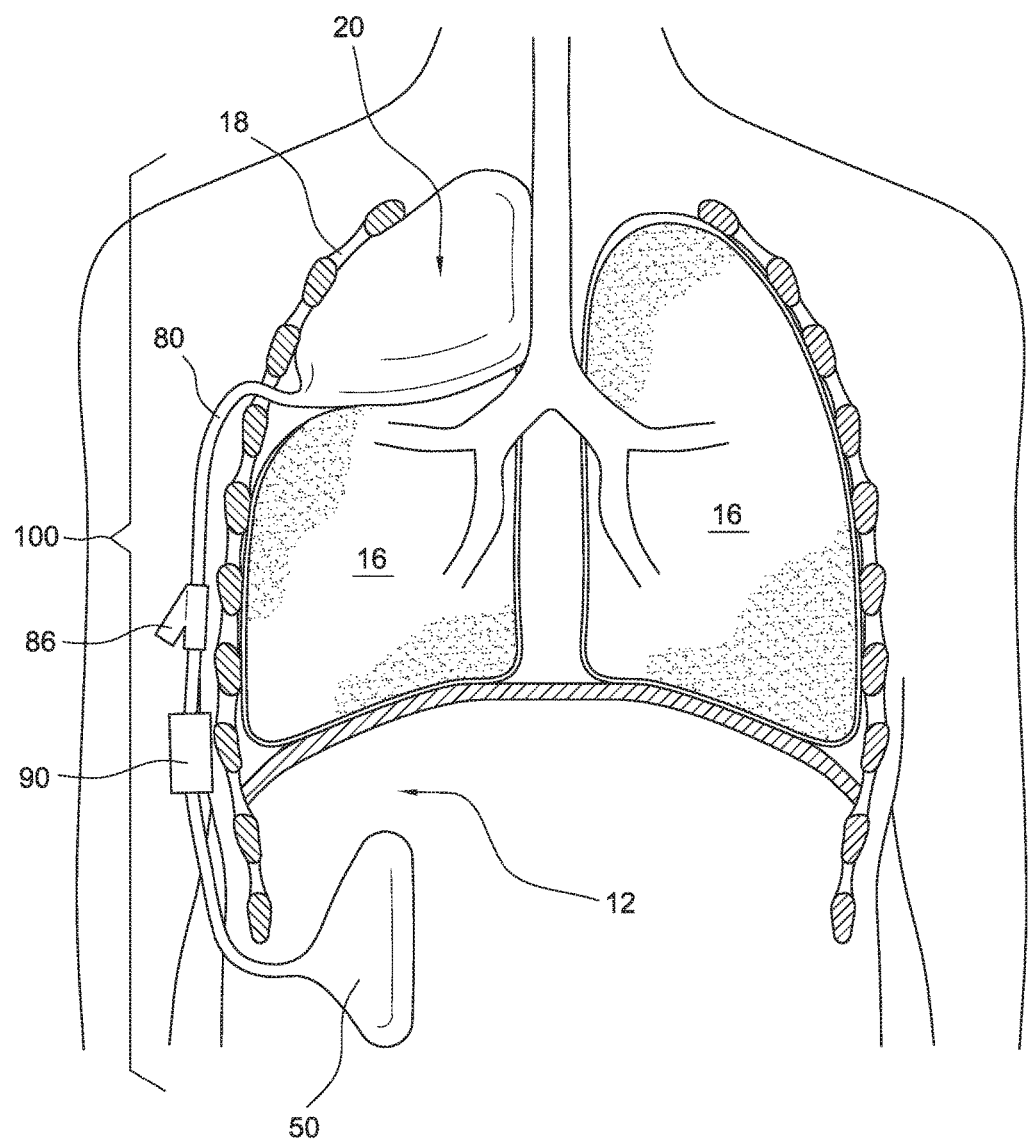
FIG. 3 shows a front view of the dual chamber breathing prosthesis according to various embodiments implanted into a human patient.

Referring initially to FIG. 3, a dynamic dual chamber breathing prosthesis 100 of the present teachings is shown after having been surgically implanted into a patient. The dual chamber breathing prosthesis 100 includes an elastic lung prosthetic 20 that can be surgically implanted in a chest cavity 18 of a patient after lung resection. The lung resection can result from, for example, a lobectomy, a segmentectomy, non-anatomic wedge resection, a pneumonectomy, and the like. The dynamic dual chamber breathing prosthesis 100 of the present teachings can also be used in the case of lung volume reduction surgery (LVRS) for patients with emphysema or other diseases affecting the lungs. Moreover, the device and methods of the present teachings can also be used for patients with emphysema without resecting any lung tissue or in cases of any respiratory disease where a space occupier is needed.

The dual chamber breathing prosthesis 100 of the present teachings also includes a separate reservoir 50 which can be implanted in, for example, the abdominal cavity 12 of the patient. The dual chamber breathing prosthesis 100 further includes subcutaneous tubing 80 that can connect the elastic lung prosthetic 20 with the reservoir 50.

The subcutaneous tubing 80 can include a subcutaneous access port 86 that can be accessible through the chest wall of the patient. By injecting or removing a fluid, such as a gas or a liquid, through this access port 86, a fine-tuning of the sizing of the elastic lung prosthetic 20 for an individual patient can be achieved.

According to various embodiments, the reservoir 50 could be located subcutaneously or submuscularly, such as in the subcutaneous tissue in the chest, the back, the abdominal wall, or in the axilla (i.e. the "armpit") of the patient. The reservoir 50 can also be made of an elastic material that allows it to readily change size and shape as fluid enters and exits therefrom.

Upon implantation in the patient, each of the elastic lung prosthetic 20, the reservoir 50, and the subcutaneous tubing 80 can be filled with a fluid. At the same time, air can be completely purged or removed from the system. According to various embodiments, the fluid can be a saline solution, any inert solution, and the like. According to various embodiments, the gas can be air, helium, carbon dioxide, or any inert gas.

In the dual chamber breathing prosthesis 100 of the present teachings, the main elastic lung prosthetic 20 can define a relatively large chamber in the area of the chest cavity 18 and the reservoir 50 can define a relatively small chamber in the area of the abdominal cavity 12. Each of the elastic lung prosthesis 20 and the elastic reservoir 50 can function similar to paired elastic balloons in that they can alternate increasing and decreasing in size as fluid flows in either direction through the subcutaneous tubing 80. In use, a dynamic alternation in size occurs automatically by way of forces acting on the components of the dual chamber breathing prosthesis 100 created by the inspiration and expiration of air by the patient during normal respiration.

When implanted, the elastic lung prosthesis 20 occupies the thoracic cavity (i.e. the chest cavity) and can be arranged adjacent to the native lung tissue and in direct or indirect contact therewith. As the elastic lung prosthesis 20 changes shape as discussed in more detail below with reference to FIGS. 4 and 5, it prevents the remaining lung (or lobe(s)) from hyper-expanding. In this way, the elastic lung prosthesis 20 behaves as a dynamic space occupier in the chest cavity thereby helping to restore the normal size, shape, and mechanics of the remaining native lung tissue and allows for more normal respiration to be achieved.

Now referring to FIGS. 4 and 5, the ability of the elastic lung prosthetic 20 to alter in size and mimic the change in size and shape of a real lung in an expanding and contracting chest cavity will now be described.

Figure 4:
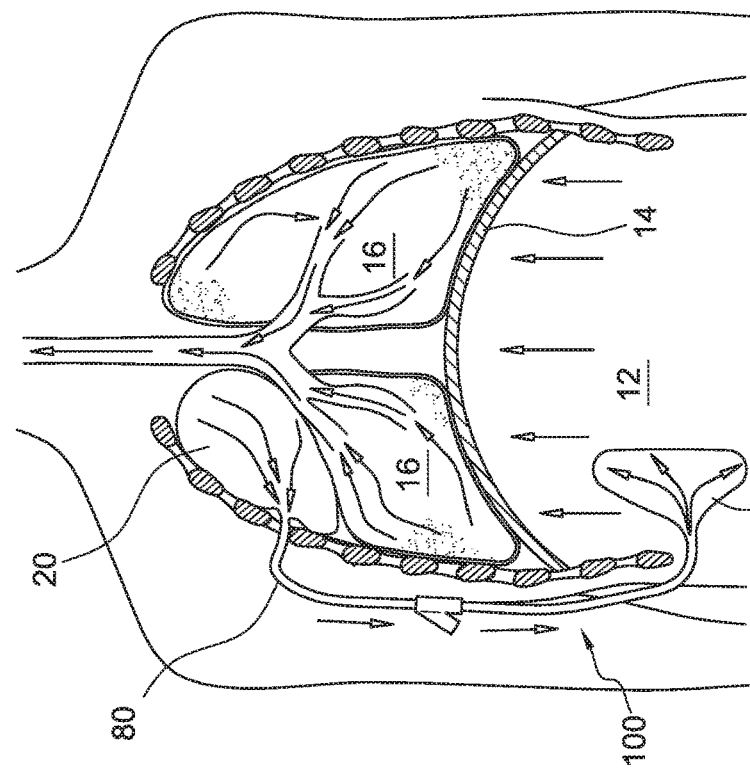
FIG. 4 shows a front schematic view of an implanted dual chamber breathing prosthesis according to various embodiments during inspiration by the patient.

FIG. 4 shows the expansion of the elastic lung prosthetic 20 during the initial inspiration of air into the lungs 16 by the patient. As the patient breathes in, the muscle of the diaphragm 14 contracts and moves downward. At the same time, the chest and rib muscles contract and cause the ribs to spread outward. These muscle contractions cause the chest cavity to expand allowing air to rush into the lungs from the mouth and nose of the patient. Concurrently, the expanding chest cavity creates an expansion force by way of a vacuum on the elastic walls of the lung prosthetic 20 which forces fluid to rush into the lung prosthetic 20 from the reservoir 50 situated in the abdominal cavity 12. The increase in size of the lung prosthetic 20 mimics a real lung expanding with air since the amount of fluid that is forced into the lung prosthetic 20 of the dual chamber breathing prosthesis 100 of the present teachings is in direct relationship to the amount of air that the patient breathes into the remaining lungs.

Figure 5:
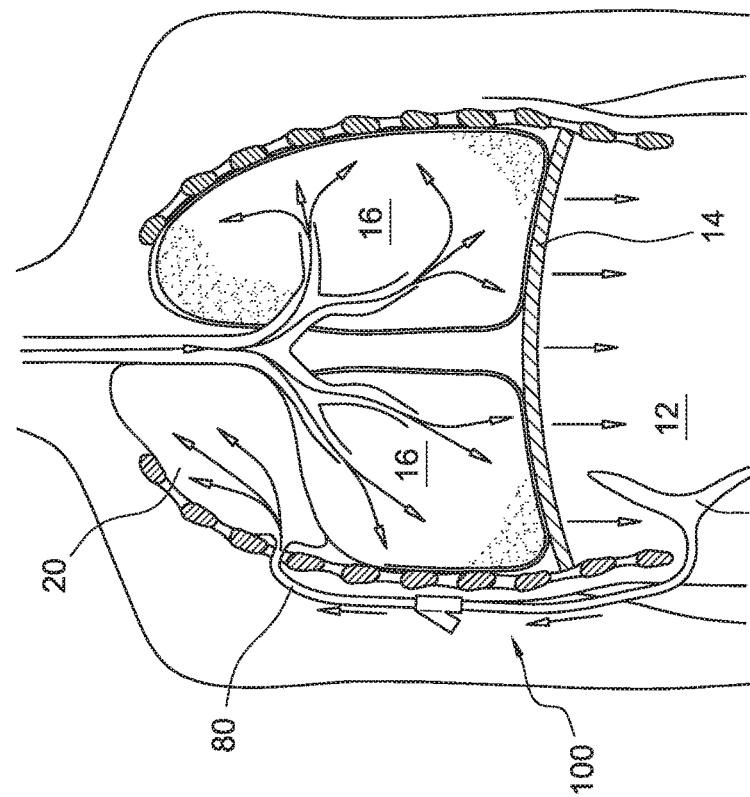
FIG. 5 shows a front schematic view of an implanted dual chamber breathing prosthesis according to various embodiments during expiration by the patient.

FIG. 5 shows the contraction of the elastic lung prosthetic 20 during the subsequent expiration of the air from the lungs 16 by the patient. As a patient breathes out, the muscle of the diaphragm 14 relaxes and the diaphragm 14 bows upward. At the same time, the chest and rib muscles relax which causes the ribs to retract inward causing the chest cavity to shrink in size. The relaxing of the muscles and the upward bow of the diaphragm 14 causes air to rush out of the lungs 16 and through the mouth and nose of the patient. Concurrently, the contracting chest cavity creates a contracting force on the elastic walls of the lung prosthetic 20 which forces fluid to rush out of the lung prosthetic 20 and into the reservoir 50 situated in the abdominal cavity 12. The decrease in size of the lung prosthetic 20 mimics a real lung expiring air since the amount of fluid that is forced out of the lung prosthetic 20 of the dual chamber breathing prosthesis 100 of the present teachings is in direct relationship to the amount of air that the patient breathes out.

Moreover, even more fluid can move from the reservoir 50 to the lung prosthetic 20 or from lung prosthetic 20 to reservoir 50 with deep inspiration or deep expiration, respectively. This can correspond to respirations that exceed the normal tidal volume and enter into the inspiratory reserve volume and the expiratory reserve volume of the respiratory cycle respectively (see FIG. 2).

Figure 1:
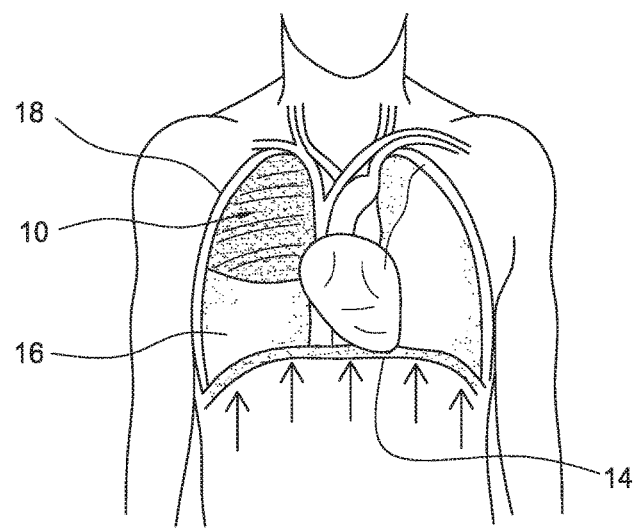
FIG. 1 shows a front cutaway view of a human showing the heart and lungs of a patient after removal of an unhealthy lung lobe.
Figure 2:
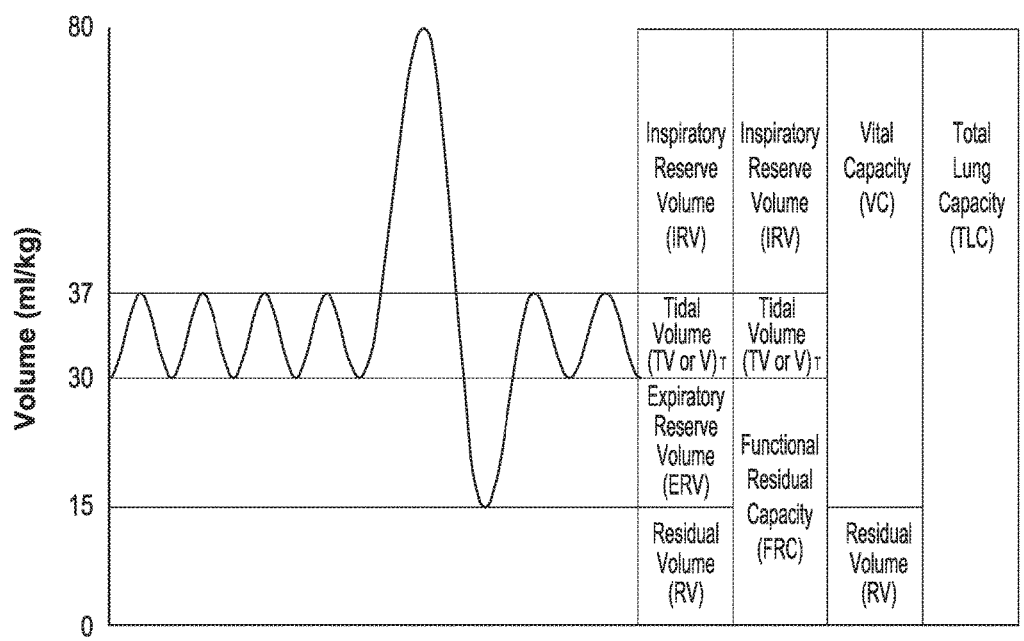
FIG. 2 shows a standard spirometry chart depicting lung volumes.

As a breathing cycle of inspiration and expiration alternatingly occurs during normal respiration, each of the elastic lung prosthetic 20 and the reservoir 50 takes turns inflating and deflating as described above and shown in FIGS. 4 and 5. The dynamic dual chamber breathing prosthesis 100 of the present teachings is arranged to allow the elastic lung prosthetic 20 to dynamically change its size with inspiration and expiration by allowing a fluid to freely flow therein to inflate the lung prosthetic 20 and then to flow out to deflate the lung prosthetic 20 with each breathing cycle. The reservoir 50 in the abdominal cavity provides a place to store the extra fluid during the expiration phase of normal respiration. This extra fluid will flow back and forth between the reservoir 50 in the abdominal cavity 12 and the main body of the elastic lung prosthetic 20 implanted in the chest cavity. This "extra" gas or fluid that exchanges back and forth between the lung prosthetic 20 and the reservoir 50 corresponds to the tidal volume on the standard spirometry chart (FIG. 2).

The dynamic dual chamber breathing prosthesis 100 of the present teachings can thereby improve pulmonary function of a native lung during normal respiration of a patient after a lung resection surgery. When implanted with an emphysematous lung, the dynamic dual chamber breathing prosthesis 100 of the present teachings can also improve the pulmonary function of the emphysematous lung during normal respiration without the need for lung resection surgery.

Referring to FIG. 3, the dual chamber breathing prosthesis 100 of the present teachings can include a motorized pump 90 that can be arranged to help move fluid between the lung prosthetic 20 and the reservoir 50 with every respiration. The motorized pump 90 can be implanted and can be arranged in fluid communication with the fluid circuit including the lung prosthetic 20, the reservoir 50, the tubing 80, and the access port 86. The motorized pump 90 can include a sensor that detects changes in respiration. For example, the sensor of the motorized pump 90 can sense movement of the chest wall, diaphragm muscle, and/or rib movement. The sensor of the motorized pump 90 can include a pressure sensor that senses changes in intrathoracic pressure with every respiration. Based on the sensor readings, the motorized pump 90 can pump the fluid between the lung prosthetic 50 and the abdominal reservoir 50. According to various embodiments, the motorized pump 90 can be programmable and fine-tuned wirelessly.

Figure 6:
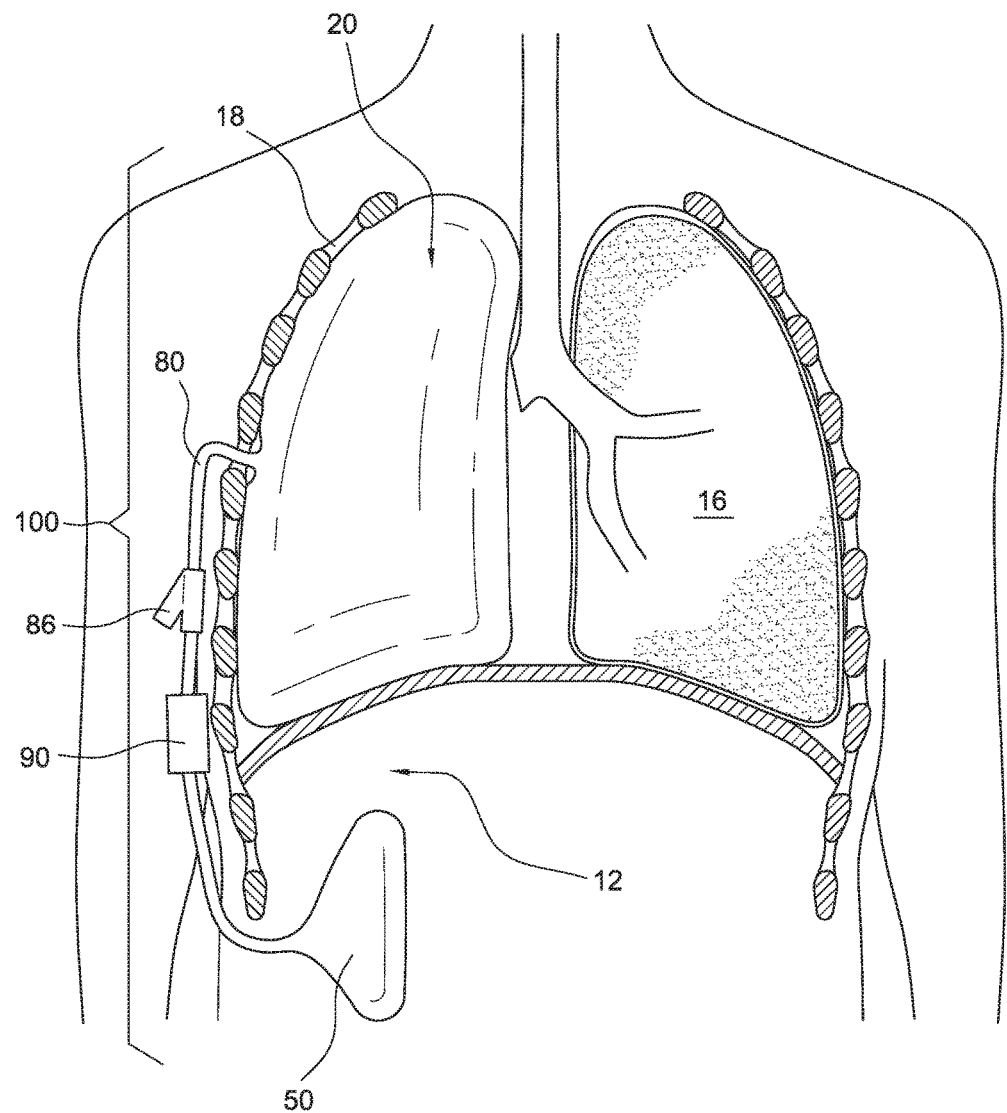
FIG. 6 shows a front view of the dual chamber breathing prosthesis according to various embodiments implanted into a human patient after an pneumonectomy.

Referring now to FIG. 6, the dual chamber breathing prosthesis 100 of the present teachings is shown being used in a patient that has had a pneumonectomy. According to this embodiment, the elastic lung prosthetic 20 is sized to replace the entire resected lung and is shown implanted in the chest cavity 18. Similarly as described above with respect to FIGS. 4 and 5, as a breathing cycle of inspiration and expiration alternatingly occurs during normal respiration, each of the full-sized elastic lung prosthetic 20 and the reservoir 50 take turns dynamically inflating and deflating by allowing a fluid to freely flow therebetween with each breathing cycle.

The dynamic dual chamber breathing prosthesis 100 of the present teachings can be implanted using one or more surgeries. One option can include a single stage operation whereby at the time of an original lobectomy surgery or as part of an original lung resection procedure, the dual chamber prosthesis can be completely implanted. The dynamic dual chamber breathing prosthesis 100 of the present teachings can also be implanted in a single stage surgery to treat emphysema without any lung resection.

Another option is to perform two surgeries spaced apart by a period of time, such as spaced apart by a few weeks or about a month. In the first surgery, at the time of lung resection, a temporary implant can be placed in the chest cavity that is an exact replica in size and shape of the final lung prosthetic 20 and is infection resistant. The temporary implant can be composed of bioprosthetic material and can be implanted in the chest cavity during the first surgery in order to create a space for the final lung prosthetic 20 that would be placed at a later date. This temporary implant can be later removed (e.g. after about 2 to 4 weeks) at which time the permanent elastic lung prosthetic 20 is implanted. This will allow time for the remaining lung tissue to heal from the original lung resection and for any potential infectious issues to become resolved. Then, in a second surgery the temporary implant is removed and the dual chamber breathing prosthesis 100 is implanted permanently.

According to various embodiments, the lung prosthetic 20 can include relatively small attachment hooks or barbs on its surface which can allow the surgeon to attach the elastic lung prosthetic 20 to the inner chest wall so as to minimize or prevent movement of the elastic lung prosthetic 20 in the chest cavity.

The components of the dual chamber breathing prosthesis 100 of the present teachings can be made from a lightweight plastic or from a rubber-like material, such as silastic. The dual chamber breathing prosthesis 100 can be coated with an infection-resistant coating that can be antibiotic-impregnated. The dual chamber breathing prosthesis 100 could also be covered with a biologic covering, such as a porcine or bovine-derived material, that resorbs with time and is incorporated into the surrounding tissues.

The elastic lung prosthetic 20 and the other components of the dual chamber breathing prosthesis 100 can be personally sized based on the physical characteristics of each patient. For example, initial sizing of these components could be based upon radiographic measurements of the patient taken from 3-D reconstructions from computed scintigraphy (e.g. a CT scan). The elastic lung prosthetic 20 could be made using 3-D printing of any other known manufacturing process as would be appreciated by one of ordinary skill in the art. The same techniques can be implemented for the sizing and manufacture of the reservoir 50 and other parts of the dynamic dual chamber breathing prosthesis 100 of the present teachings.

According to various embodiments, the tubing 80 can include a single lumen and not include a valve within the lumen. Such a valveless lumen can allow fluid to flow freely in both directions between the elastic lung prosthesis 20 and the reservoir 50 based upon the phase of breathing during normal respiration.

The single lumen tubing 80 can be employed with a double-valve or two-way valve mechanism that can be constructed either within the single lumen, or at the juncture of the access port 86. The double-valve or two-way valve mechanism can be arranged within the lung prosthetic 20 or within the reservoir 50 at the junction where the subcutaneous tubing 80 enters the lung prosthetic 20 or the reservoir 50.

Alternatively, the tubing 80 can include a double lumen including a one-way valve arranged in each lumen. The first lumen of the tubing 80 could be arranged to allow fluid to flow from the reservoir 50 to the elastic lung prosthetic 20 while the second lumen could be arranged to allow the fluid to flow from the elastic lung prosthetic 20 to the reservoir 50.

Those skilled in the art can appreciate from the foregoing description that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

What is claimed is:

1. A dual chamber breathing prosthesis comprising:
    an elastic lung prosthetic having a variable volume and capable of being implanted in a chest cavity of a patient in place of an excised lobe;
    an elastic reservoir having a variable volume and capable of being implanted in the patient; and
    a tube arranged between the elastic lung prosthetic and the reservoir such that the elastic lung prosthetic is in fluid communication with the reservoir;
    wherein the elastic lung prosthetic and the elastic reservoir are configured to alternate increasing and decreasing in volume by way of a fluid being dynamically transferred between the elastic lung prosthetic and the elastic reservoir during a repetition by the patient of a breathing cycle including an inspiration phase and an expiration phase.

2. The dual chamber breathing prosthesis of claim 1, wherein the elastic lung prosthetic is configured to increase in volume while the reservoir is configured to decrease in volume as fluid is transferred into the elastic lung prosthetic from the reservoir during the inspiration phase of each breathing cycle.

3. The dual chamber breathing prosthesis of claim 2, wherein the elastic lung prosthetic is configured to increase in volume by a force on the elastic lung prosthetic created by expansion of the chest cavity during the inspiration phase.

4. The dual chamber breathing prosthesis of claim 2, wherein the elastic lung prosthetic is configured to decrease in volume while the reservoir is configured to increase in volume as fluid is transferred into the elastic reservoir from the elastic lung prosthetic during the expiration phase of each breathing cycle.

5. The dual chamber breathing prosthesis of claim 4, wherein the elastic lung prosthetic is configured to decrease in volume by a force on the elastic lung prosthetic created by contraction of the chest cavity during the expiration phase.

6. The dual chamber breathing prosthesis of claim 1, wherein the elastic reservoir is capable of being implanted in the abdominal cavity.

7. The dual chamber breathing prosthesis of claim 1, wherein the tube is capable of being implanted subcutaneously in the patient.

8. The dual chamber breathing prosthesis of claim 7, wherein the tube includes an access port configured to allow the fluid to be injected or removed from the breathing prosthesis.

9. The dual chamber breathing prosthesis of claim 1, further including a motorized pump operatively arranged to transfer the fluid between the elastic lung prosthetic and the elastic reservoir during each breathing cycle.

10. A dual chamber breathing prosthesis device capable of dynamically changing in volume during a breathing cycle of a patient defined by an inspiration phase and an expiration phase comprising:
    an elastic lung prosthetic having a variable volume and capable of being implanted in a chest cavity of the patient;
    an elastic reservoir having a variable volume and capable of being implanted in the patient; and
    a tube configured to place the elastic lung prosthetic in fluid communication with the elastic reservoir;
    wherein during each breathing cycle the elastic lung prosthetic is configured to dynamically change in volume whereby during the inspiration phase the elastic lung prosthetic increases in volume and during the expiration phase the elastic lung prosthetic decreases in volume.

11. The dual chamber breathing prosthesis device of claim 10, wherein the elastic lung prosthetic is configured to dynamically change in volume during each breathing cycle by way of a fluid being configured to flow into and inflating the elastic lung prosthetic and then subsequently flowing out of and deflating the elastic lung prosthetic.

12. The dual chamber breathing prosthesis of claim 11, wherein the elastic lung prosthetic is configured to increase in volume by a force on the elastic lung prosthetic created by expansion of the chest cavity during the inspiration phase.

13. The dual chamber breathing prosthesis of claim 12, wherein the elastic lung prosthetic is configured to decrease in volume by a force on the elastic lung prosthetic created by contraction of the chest cavity during the expiration phase.

14. The dual chamber breathing prosthesis of claim 10, wherein the reservoir is capable of being implanted in the abdominal cavity.

15. The dual chamber breathing prosthesis of claim 10, wherein the tube is capable of being implanted subcutaneously in the patient.

16. The dual chamber breathing prosthesis of claim 15, wherein the tube includes an access port configured to allow the fluid to be injected or removed from the breathing prosthesis.

17. The dual chamber breathing prosthesis of claim 10, further including a motorized pump operatively arranged to transfer the fluid between the elastic lung prosthetic and the reservoir during each breathing cycle.

18. A surgical method for improving pulmonary function of a remaining native lung during normal respiration of a patient after a lung resection surgery comprising:
    implanting an elastic lung prosthetic having a variable volume in a chest cavity of the patient adjacent the remaining native lung;
    implanting an elastic reservoir having a variable volume in the patient;
    providing a tube to arrange the elastic lung prosthetic in fluid communication with the elastic reservoir; and
    providing a fluid within the reservoir and allowing a dynamic change in volume of the elastic lung prosthetic by the fluid transferring from the elastic reservoir into the elastic lung prosthetic by a force created by an inspiration phase of respiration by the patient and then transferring the fluid from the elastic lung prosthetic back into the elastic reservoir by a force created by an expiration phase of respiration by the patient.

19. The method of claim 18, wherein allowing a dynamic change in volume of the elastic lung prosthetic includes configuring the elastic lung prosthetic to receive an expansion force by an expansion of the chest cavity by the patient during the inspiration phase thereby transferring the fluid into the elastic lung prosthetic from the elastic reservoir.

20. The method of claim 19, wherein allowing the dynamic change in volume of the elastic lung prosthetic includes configuring the elastic lung prosthetic to receive a contraction force by a contraction of the chest cavity by the patient during the expiration phase thereby transferring the fluid out of the elastic lung prosthetic and into the elastic reservoir.

21. A surgical method for improving pulmonary function of an emphysematous lung during normal respiration of a patient comprising:
    implanting an elastic lung prosthetic having a variable volume in a chest cavity of the patient adjacent the emphysematous lung;
    implanting an elastic reservoir having a variable volume in the patient;
    providing a tube to arrange the elastic lung prosthetic in fluid communication with the elastic reservoir; and
    providing a fluid within the reservoir and allowing a dynamic change in volume of the elastic lung prosthetic by the fluid transferring from the elastic reservoir into the elastic lung prosthetic by a force created by an inspiration phase of respiration by the patient and then transferring the fluid from the elastic lung prosthetic back into the elastic reservoir by a force created by an expiration phase of respiration by the patient.

22. The method of claim 21, wherein allowing a dynamic change in volume of the elastic lung prosthetic includes configuring the elastic lung prosthetic to receive an expansion force by an expansion of the chest cavity by the patient during the inspiration phase thereby transferring the fluid into the elastic lung prosthetic from the elastic reservoir.

23. The method of claim 22, wherein allowing the dynamic change in volume of the elastic lung prosthetic includes configuring the elastic lung prosthetic to receive a contraction force by a contraction of the chest cavity by the patient during the expiration phase thereby transferring the fluid out of the elastic lung prosthetic and into the elastic reservoir.

24. A surgical method for improving pulmonary function during normal respiration of a patient after a pneumonectomy comprising:
    implanting an elastic lung prosthetic having a variable volume in a chest cavity of the patient where the pneumonectomy occurred;
    implanting an elastic reservoir having a variable volume in the patient;
    providing a tube to arrange the elastic lung prosthetic in fluid communication with the elastic reservoir; and
    providing a fluid within the reservoir and allowing a dynamic change in volume of the elastic lung prosthetic by the fluid transferring from the elastic reservoir into the elastic lung prosthetic by a force created by an inspiration phase of respiration by the patient and then transferring the fluid from the elastic lung prosthetic back into the elastic reservoir by a force created by an expiration phase of respiration by the patient.

25. A dual chamber breathing prosthesis comprising:
    an elastic lung prosthetic capable of being implanted in a chest cavity of a patient in place of an excised lobe;
    a reservoir capable of being implanted in the patient; and
    a tube configured to be operatively arranged between the elastic lung prosthetic and the reservoir such that the elastic lung prosthetic is in fluid communication with the reservoir; and
    a motorized pump operatively arranged to transfer the fluid between the elastic lung prosthetic and the reservoir during each breathing cycle;
    wherein as a breathing cycle comprising an inspiration phase and an expiration phase alternatingly occurs during normal respiration a fluid is capable of being dynamically transferred between the elastic lung prosthetic and the reservoir during each breathing cycle.

26. A dual chamber breathing prosthesis device capable of dynamically changing in size during a breathing cycle of a patient defined by an inspiration phase and an expiration phase comprising:
    an elastic lung prosthetic capable of being implanted in a chest cavity of the patient;
    an elastic reservoir capable of being implanted in the patient;
    a tube configured to place the elastic lung prosthetic in fluid communication with the elastic reservoir; and
    a motorized pump operatively arranged to transfer the fluid between the elastic lung prosthetic and the reservoir during each breathing cycle;
    wherein during each breathing cycle the elastic lung prosthetic is configured to dynamically change in size whereby during the inspiration phase the elastic lung prosthetic increases in size and during the expiration phase the elastic lung prosthetic decreases in size.

\* \* \* \* \*